United States Patent [19]

Baur et al.

[11] Patent Number: 5,763,643
[45] Date of Patent: Jun. 9, 1998

[54] PREPARATION OF ALKYL ESTERS OF (METH)ACRYLIC ACID

[75] Inventors: Karl Gerhard Baur, Ludwigshafen; Ulrich Annen, Hassloch; Herbert Exner, Waldsee; Michael Fried, Heidelberg; Ulrich Rauh, Limburgerhof, all of Germany

[73] Assignee: BASF Aktiengesellschaft, Ludwigshafen, Germany

[21] Appl. No.: 708,722

[22] Filed: Sep. 5, 1996

[30] Foreign Application Priority Data

Sep. 28, 1995 [DE] Germany .................. 195 36 183.0

[51] Int. Cl.$^6$ .................................................. C07C 67/30
[52] U.S. Cl. .................................................. 560/212
[58] Field of Search ..................................... 560/212

[56] References Cited

U.S. PATENT DOCUMENTS 3,836,575  9/1974  Bouniot .................... 560/212

FOREIGN PATENT DOCUMENTS

| 1 058 390 | 2/1992 | China . |
| 1 063 678 | 8/1992 | China . |
| 47-15936 | 5/1972 | Japan . |
| 57-62229 | 4/1982 | Japan . |
| 5-25086 | 2/1993 | Japan . |
| 6-65149 | 3/1994 | Japan . |
| 7207382 | 12/1972 | Netherlands . |
| 923 595 | 4/1963 | United Kingdom . |

*Primary Examiner*—Paul J. Killos
*Attorney, Agent, or Firm*—Oblon, Spivak, McClelland, Maier & Neustadt, P.C.

[57] ABSTRACT

A process for the preparation of $C_1$–$C_4$-alkyl esters of (meth)acrylic acid from esters of the formula I

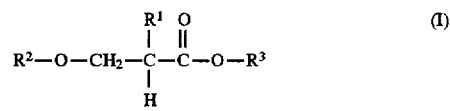

and in case from esters of the formula (II)

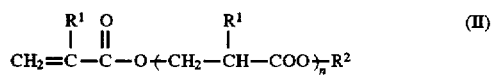

where
$R^1$ is hydrogen or —$CH_3$,
$R^2$ and $R^3$ are each $C_1$–$C_4$-alkyl, and
n is an integer $\geq 0$,
in the liquid phase and in the presence of an acid at reduced pressure and with continuous removal of the cleavage products.

10 Claims, No Drawings

PREPARATION OF ALKYL ESTERS OF (METH)ACRYLIC ACID

The present invention relates to a process for the preparation of alkyl esters of (meth)acrylic acid by eliminating alcohol from alkyl esters of β-acryloxy- or β-alkoxypropionic acid or -isobutyric acid.

In the course of the acid-catalyzed preparation of $C_1$–$C_4$-alkyl esters of (meth)acrylic acid, compounds of the general formula I and in case those of the general formula II are formed as byproducts.

The present invention relates in particular to a process for the preparation of $C_1$–$C_4$-alkyl esters of (meth)acrylic acid ((meth)acrylic acid is acrylic or methacrylic acid) by eliminating the alcohol $R^2$—OH from esters of the general formula I

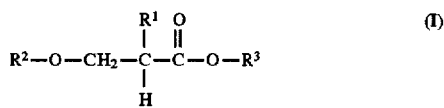

where
$R^1$ is hydrogen or —$CH_3$ and
$R^2$ and $R^3$ are each $C_1$–$C_4$-alkyl,
in the liquid phase and in the presence of an acid according to the following equation:

and in case by correspondingly eliminating of (meth)acrylic acid from esters of the general formula II

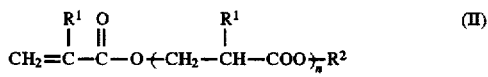

where
$R^1$ is hydrogen or —$CH_3$,
$R^2$ is $C_1$–$C_4$-alkyl and
n is an integer $\geq 0$.

This means that unconverted alcohol and unconverted (meth)acrylic acid are also capable of undergoing addition at the double bond of alkyl (meth)acrylate already formed and according to the invention are eliminated according to the above reaction.

$C_1$–$C_4$-Alkyl esters of (meth)acrylic acid are generally known. They are important starting monomers for the preparation of polymers which are used, for example in the form of their aqueous dispersion, as binders in a wide range of applications.

$C_1$–$C_4$-Alkyl esters of (meth)acrylic acid are usually prepared by esterifying (meth)acrylic acid with $C_1$–$C_4$-alkanols in the liquid phase and in the presence of an acid as a catalyst (cf. for example DE-A 23 39 519). The disadvantage of this method of preparation is that, as a secondary reaction under the abovementioned esterification conditions, unconverted starting alcohol undergoes addition (Michael addition) at the double bond of already formed alkyl (meth)acrylate with formation of a compound of the general formula I, with the result that the formation of desired product is reduced.

EP-A 379 691 and EP-A 429 800 disclose that alkyl (meth)acrylates can be produced by elimination of alcohol from alkyl esters of βalkoxyalkanecarboxylic acids in the gas phase over crystalline zeolites. The disadvantage of this procedure is that it has to be carried out in the gas phase. The latter requires, for example, the use of comparatively complex tube reactors or tube bundle reactors. In the same way, German Published Applications DE-AS 1,126,378, DE-AS 1,124,481, DE-AS 1,124,482 and DE-AS 1,124,483 relate to the cleavage of β-alkoxymonocarboxylates with the use of a very wide range of acidic catalysts in the gas phase.

German Published Application DE-AS 2,339,519, JP-A 05/25086, JP-B 72/38419 and CN-A 1 058 390 relate to the recleavage of alkyl β-alkylpropionates in the liquid phase in the presence of acids, such as P-toluenesulfonic acid, sulfuric acid or phosphoric acid, as catalysts and with the use of pressures $\geq 1$ atm. The disadvantage of this procedure is that a large amount of the alcohol eliminated reacts further to form the corresponding dialkyl ether, with the result that, on the one hand, alcohol to be esterified is removed also on recycling the cleavage product mixture to the esterification thereof and, on the other hand, the preparation of the alkyl (meth)acrylate is contaminated with dialkyl ether. Thus, in a separation of the dialkyl ether from the esterification product mixture by rectification, as a rule a not inconsiderable amount of alkyl acrylate, ie. the desired ester, is entrained. In contrast, the novel process results in reduced dialkyl ether formation.

U.S. Pat. No. 4,814,492 discloses the recleavage of $C_1$–$C_5$-alkyl esters of methoxypropionic acid into the corresponding alkyl acrylates over base-treated zeolites in a fixed bed and with the use of superatmospheric pressure for maintaining the liquid state of aggregation. According to the exemplary embodiment of U.S. Pat. No. 4,814,492, the alcohol eliminated is absorbed in the fixed-bed catalyst.

The disadvantage of this procedure is the complicated handling of the fixed-bed catalyst, which, for example owing to polymer formation occurring as the secondary reaction, becomes blocked from time to time and has to be changed.

Cleavage processes which have disadvantages similar to those of the abovementioned cleavage processes are disclosed in CN-A 1 063 678, GB 923 595, JP-A 82/6229, Japanese Published Application 72/15936 and JP-A 94/65149.

It is an object of the present invention to provide a process which avoids the disadvantages of the known processes and in particular reverses the abovementioned Michael addition with reformation of desired alkyl (meth)acrylate and starting alcohol. The object in particular was to provide a cleavage process whose product mixture as such can be recycled directly to the esterification stage to increase the yield of alkyl (meth)acrylate without substantially impairing said stage and the working up of the resulting product mixture.

Against the background of the abovementioned prior art, we have found that this object is achieved, according to the invention, by a process for the preparation of $C_1$–$C_4$-alkyl esters of (meth)acrylic acid from esters of the general formula I

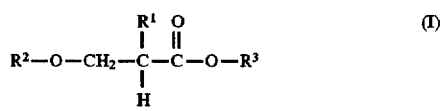

and in case from esters of the formula (II)

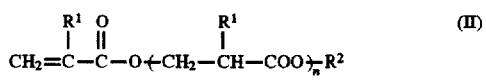

where
$R^1$ is hydrogen or —$CH_3$,
$R^2$ and $R^3$ are each $C_1$–$C_4$-alkyl, and n is an integer $\geq 0$, in the liquid phase and in the presence of an acid, at reduced pressure (<1 atm) and with continuous removal of the cleavage products.

Preferably $R^2$ and $R^3$ are identical.

The use of the novel process is particularly important in the case of compounds I in which $R^2$ and $R^3$ are each $C_4$-alkyl, in particular n-butyl. Under the abovementioned preconditions, $R^1$ is advantageously at the same time H.

The use of the novel process in the case of n-butyl β-n-butoxypropionate as compound (I) and n-butyl β-acryloxypropionate as compound (II) is very particularly advantageous.

Catalytically active acids which are suitable according to the invention are both Lewis acids and Brönsted acids. The latter are compounds capable of donating a proton to a Brönsted base. The former are compounds which have an acceptor site for electron pairs. Examples of Lewis acids are the trihalides of the third main group, such as $BF_3$ or $AlCl_3$. Preferably, the catalytically active acids are soluble, in the amount to be used, in the compound under the reaction conditions. However, finely divided solid acids are also suitable. Examples of these are alumina and zirconium dioxide. Particularly suitable Brönsted acids are the strong protic mineral acids. Examples are sulfuric acid, phosphoric acid, methanesulfonic acid, benzenesulfonic acid, dodecylbenzenesulfonic acid and p-toluenesulfonic acid. A sparingly volatile mineral acid is preferably used. Acidic ion exchange resins, for example sulfo-containing resins, may also be used as catalysts in a form distributed in the reaction mixture.

The amount of catalytically active acid to be used depends, in a manner known per se to a person skilled in the art, on the type and strength of the acid. In the case of p-toluenesulfonic acid, advantageously from 1 to 20, preferably from 5 to 15, particularly preferably from 5 to 10, % by weight, based on the amount of the compound I and, if any, compound II to be cleaved, are used. Other strong acids are to be used in comparable amounts. Preferably, the novel process is carried out in the absence of an inert solvent.

The operating pressure of the novel process is advantageously from 100 to 900, preferably from 200 to <500, particularly preferably from 200 to 400, mbar. The operating temperature is as a rule from 120° to 220° C., preferably from 160° to 220° C., particularly preferably from 180° to 200° C. It is advantageously below the boiling point $T_b$ of the reaction mixture at the chosen operating pressure. The following is advantageously applicable to the operating temperature $T_O$ of the novel process:

$$T_b - 10° C. < T_O < T_b.$$

The novel process is advantageously carried out in a simple stirred kettle. Since the boiling points of the cleavage products are substantially lower than the boiling point of the starting compound to be cleaved, the cleavage products (the alcohol and the (meth)acrylate, in case also (meth)acrylic acid) are present in higher concentration in the gas phase in equilibrium with the liquid phase, relative to said liquid phase. By continuously separating off the gas phase, the cleavage products can therefore be removed from the reaction system in a simple manner.

The separation efficiency can be increased in a simple manner by connecting, between the stirred kettle and the removal point, a rectification apparatus whose reflux ratio is established, in a manner known per se to a person skilled in the art, so that essentially exclusively the cleavage products are removed. Examples of suitable rectification apparatuses of this type are the rectification columns known per se, for example packed or plate columns.

The novel process is preferably carried out continuously, ie. compound of the general formula I and in case II which is to be cleaved is fed continuously to the stirred kettle at the rate at which cleavage products are continuously removed. A dwell container coupled to a forced-circulation evaporator (eg. falling-film evaporator or flash evaporator) is advantageously used. It is noteworthy that the novel procedure reduces not only the amount of dialkyl ether formed from the eliminated alcohol in a secondary reaction. Rather, it also reduces the amount of alkene formed from the eliminated alcohol by dehydration in a further secondary reaction.

The cleavage products continuously removed in this manner can be recycled directly to the esterification.

The process according to the invention is particularly advantageous in the acid-catalyzed esterification of n-butanol with acrylic acid. This is preferably carried out at atmospheric or reduced pressure using a temperature from 80° to 135° C. and a small excess of n-butanol. As a rule, the molar ratio of n-butanol to acrylic acid is 1.1:1. The esterification is carried out in the presence of from 1 to 5% by weight, based on the reactants, of, for example, sulfuric acid as a catalyst and with the use of a conventional low-boiling azeotropic entraining agent for removing the resulting water of reaction in a stirred kettle cascade. Frequently, the product mixture obtained in the esterification contains up to 10% by weight of compounds I and compounds II. Typically, the compounds II, as in the case of the compounds I, also have a higher boiling point compared with the other components of the esterification mixture. The product mixture of the esterification is therefore usually worked up by separating the catalytically active acid by extraction with water, then extracting unconverted (meth)acrylic acid by means of aqueous alkaline solution and then separating off the entraining agent by rectification. Byproducts (eg. dialkyl ethers) having a lower boiling point than the alkyl (meth)acrylate are then removed by rectification, after which the actual desired product, the alkyl (meth)acry- late, is separated off by rectification and the bottom product consisting mainly of compounds I and II is removed.

It is noteworthy that the bottom product as such can now be fed to the novel cleavage process, since this not only results in reconversion of the compounds I into alkyl (meth)acrylate and alcohol but also converts the compounds II back into (meth)acrylic acid, alkyl (meth)acrylate and in case alcohol.

This advantage of the novel process is displayed in particular in the preparation of n-butyl acrylate, where typical bottom liquids obtained contain $\geq 50\%$ by weight (as a rule from 50 to 60% by weight) of butyl butoxypropionate and $\geq 20\%$ by weight (as a rule from 20 to 30% by weight) of butyl acryloxypropionate, which, when the novel process is used, can be converted back into the desired products n-butanol, acrylic acid and n-butyl acrylate without significant losses via secondary reactions and as such can be recycled to the esterification.

The novel process is used, as in the case of the actual esterification reaction, in the presence of usual amounts of conventional polymerization inhibitors, such as phenothiazine, hydroquinone monomethyl ether or hydroquinone.

Finally, it should be stated that the novel process can be improved by adding up to 30, as a rule from 0.5 to 25, % by weight, based on the weight of the reaction mixture, of water to the reaction mixture. This results in particular in an increased space-time yield of cleavage product.

The invention also relates to a process for the preparation of a $C_1$–$C_4$-alkyl ester of (meth)acrylic acid by acid-catalyzed esterification of a $C_1$–$C_4$-alkanol with (meth)acrylic acid, which comprises separating off the compounds of the formula I and of the formula II which are formed as byproducts from the product mixture, subjecting their mixture of the process according to the invention and recycling the cleavage products to be removed continously to the esterification.

The Example described below reveals further details and advantages of the invention.

EXAMPLE

A 2 l stirred double-jacket container was half-filled with a bottom liquid obtained in the preparation of n-butyl acrylate and having the following composition: 0.5% by weight of n-butanol, 6.5% by weight of n-butyl acrylate, 56.2% by weight of n-butyl n-butoxypropionate and 21.6% by weight of n-butyl acryloxypropionate, the remainder comprising highly condensed byproducts of the ester formation and small amounts of free radical oligomers and phenothiazine as polymerization inhibitor.

To establish an inert atmosphere, 5 l/h of nitrogen were fed into the 2 l vessel. A 50×350 mm packed rectification column which contained a BX packing from Sulzer was mounted on the 2 l stirred double-jacket container. The cleavage temperature was 195° C. 9% by weight, based on the reaction mixture, of p-toluenesulfonic acid were added as the acid catalyst. A part (about 60% by weight) of the condensate obtained at the top of the rectification column was recycled to the rectification column. The other part was collected in a discharge container. For stabilization purposes, phenothiazine, as a polymerization inhibitor, was added to the condensate recycled to the rectification column, in an amount of 800 ppm, based on the weight of said condensate. The liquid level in the stirred container was kept constant by continuous addition of bottom liquid.

After an operating time of 120 hours, the content of the discharge container was analyzed by gas chromatography. The Table below shows the analytical results for 5 different operating pressures (in % by weight, based on the total amount).

TABLE

| Operating pressures [mbar] | Di-n-butyl ether | n-Butanol | Acrylic acid | n-Butyl acrylate | Butene |
| --- | --- | --- | --- | --- | --- |
| 300 | 0.27 | 19.7 | 19.3 | 60.1 | 0.44 |
| 400 | 0.55 | 16.0 | 12.1 | 70.2 | 0.14 |
| 600 | 1.04 | 11.3 | 7.5 | 78.7 | 0.86 |
| 800 | 1.16 | 12.9 | 5.5 | 79.3 | 1.10 |
| 1000 | 1.31 | 14.9 | 8.4 | 69.3 | 4.52 |

We claim:

1. A process for the preparation of $C_1$–$C_4$-alkyl esters of (meth)acrylic acid from esters of the formula I

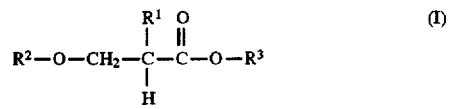

and, optionally from esters of the formula (II)

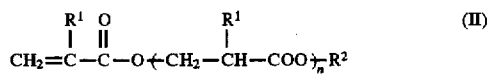

where $R^1$ is hydrogen or —$CH_3$, $R^2$ and $R^3$ are each $C_1$–$C_4$-alkyl, and n is an integer $\geq 0$, in the liquid phase and in the presence of an acid at reduced pressure and with continuous removal of the cleavage products.

2. A process as claimed in claim 1, wherein $R^2$ and $R^3$ are identical.

3. A process as claimed in claim 2, wherein $R^2$ and $R^3$ are each n-butyl.

4. A process as claimed in claim 1, wherein the compound (I) is n-butyl β-n-butoxypropionate and the compound (II) is n-butyl β-acryloxypropionate.

5. A process as claimed in claim 1, wherein p-toluenesulfonic acid is concomitantly used as the acid.

6. A process as claimed in claim 1, wherein the operating pressure is from 100 to 900 mbar.

7. A process as claimed in claim 1, wherein the operating temperature is from 120° to 220° C.

8. A process as claimed in claim 1, wherein a reaction mixture to be cleared is used which comprises at least 70% by weight, based on its total weight, of at least one compound of the formula I and at least one compound of the formula II.

9. A process as claimed in claim 1, wherein the reaction mixture to be cleaved comprises up to 30% by weight of water.

10. A process for the preparation of a $C_1$–$C_4$-alkyl ester of (meth)acrylic acid by acid-catalyzed esterification of a $C_1$–$C_4$-alkanol with (meth)acrylic acid, which comprises separating off the compounds of the formula I and of the formula II which are formed as byproducts from the product mixture, subjecting their mixture to a process as claimed in claim 1 and recycling the cleavage products to be removed continuously to the esterification.

* * * * *